United States Patent [19]

Subbiah

[11] Patent Number: 5,698,599

[45] Date of Patent: Dec. 16, 1997

[54] METHOD OF INHIBITING MYCOTOXIN PRODUCTION

[75] Inventor: Ven Subbiah, Edenton, N.C.

[73] Assignee: RJ Reynolds Tobacco Company, Winston-Salem, N.C.

[21] Appl. No.: 610,427

[22] Filed: Mar. 4, 1996

[51] Int. Cl.⁶ ............................................. A01N 35/00
[52] U.S. Cl. ..................................................... 514/703
[58] Field of Search ........................................ 514/703

[56] References Cited

U.S. PATENT DOCUMENTS

| | | | |
|---|---|---|---|
| 3,821,335 | 6/1974 | Lewis | 260/945 |
| 3,865,936 | 2/1975 | Lewis | 424/211 |
| 4,308,293 | 12/1981 | Tribble et al. | 426/532 |
| 4,780,551 | 10/1988 | Nyfeler et al. | 549/422 |
| 4,822,624 | 4/1989 | Young | 426/53 |
| 4,925,840 | 5/1990 | Nyfeler et al. | 514/228 |
| 5,068,359 | 11/1991 | Huxley et al. | 549/58 |
| 5,165,946 | 11/1992 | Taylor et al. | 426/74 |
| 5,192,547 | 3/1993 | Taylor | 424/438 |
| 5,273,996 | 12/1993 | Dickens et al. | 514/703 |

OTHER PUBLICATIONS

R.A. Andersen et al., "Nitrosation of Tobacco Alkaloids During Storage Reduced by Antimicrobial (E)–2–Hexenal Vapor", Synthesis and Chemistry of Agrochemicals IV (Sep. 16, 1994), pp. 463–472.

Wenlian Deng et al., "Effects of Six–Carbon Aldehydes and Alcohols on Bacterial Proliferation", Journal of Agricultural Food Chemistry, vol. 41 (1993), No. 3, pp. 506–510.

A.K. Mishra et al., "Fungitoxicity of Essential Oil of *Amomum subulatum* Against *Aspergillus flavus*", Economic Botany, vol. 44, pp. 530–533. (1978).

A.C. Pier et al., "Mycoses and Mycotoxicoses of Animals Caused by Aspergilli", *Aspergillus*, Biology and Industrial Applications, Butterworth–Heinemann (1992) (J.W. Bennett, Editor), pp. 233–248.

Timothy D. Phillips et al., "Selective Chemisorption and Detoxification of Aflatoxins by Phyllosilicate Clay", Natural Toxins, vol. 3 (1995), pp. 204–213.

T.R. Hamilton–Kemp et al., "Effects of Some Natural Volatile Compounds On The Pathogenic Fungi *Alternaria alternata* And *Botrytis cinerea*", Journal of Chemical Ecology, vol. 18, No. 7 (1992), pp. 1083–1091.

John E. Linz et al., "Mycotoxins: Molecular Strategies for Control", *Aspergillus*, Biology and Industrial Applications, Butterworth–Heinemann (1992) (J.W. Bennett, Editor), pp. 217–219, 228–231.

T.R. Hamilton–Kemp et al., "Effects of Lipoxygenase Inhibitors On The Formation Of Volatile Compounds In Wheat", Phytochemistry, vol. 26, No. 5 (1987), pp. 1273–1277.

Thomas R. Hamilton–Kemp et al., "Inhibition of Pollen Germination by Volatile Compounds Including 2–Hexenal and 3–Hexenal", Journal of Agricultural Chemistry, vol. 39, No. 5 (1991), pp. 952–956.

Bryce Kendrick, "Mycotoxins In Food And Feed", The Fifth Kingdom, Mycologue Publications (1985), Ontario, Canada, pp. 289–300.

Sajbidor et al, C.A., vol. 122, (1995) 122:5535a with Attachment.

*Primary Examiner*—Allen J. Robinson
*Attorney, Agent, or Firm*—Myers Bigel Sibley & Sajovec, LLP

[57] ABSTRACT

Methods of inhibiting the production of mycotoxins in plants, crops, animal feedstuffs and foodstuffs are described. Also described are methods of treating microbial infection in plants.

5 Claims, No Drawings

METHOD OF INHIBITING MYCOTOXIN PRODUCTION

FIELD OF THE INVENTION

The present invention relates to methods for inhibiting the production of mycotoxins in plants, crops, foodstuffs and animal feedstuffs. The invention also relates to methods of treating microbial infections in plants.

BACKGROUND OF THE INVENTION

Phytopathogenic microbes, including phytopathogenic bacteria and fungi, can cause serious health, agricultural and economic problems worldwide. In addition to causing infectious diseases, some phytopathogenic fungi produce toxic secondary metabolites known as mycotoxins. Mycotoxins are a chemically diverse group (e.g., steroids, carotenoids, alkaloids, cyclopeptides or coumarins) whose function in the life cycle and metabolism of the producing fungus is not currently known. Such compounds are frequently found in fungus-contaminated foodstuffs, and may remain there even after processing, sterilization or cooking. B. Kendrick, *The Fifth Kingdom* (1985).

The most studied and among the most dangerous of the mycotoxins belong to the class commonly referred to as the aflatoxins. These potent mycotoxins are, in general, produced by certain strains of the genera Aspergillus (most notably *A. flavus* and *A. parasiticus*). Aflatoxins exhibit potent hepatoxicity, mutagenicity, teratogenicity, carcinogenicity, and immunosuppression in experimental animals. The potential danger of aflatoxins to human health was initially realized in 1960 following their association with acute hepatoxicity in poultry (Turkey X disease) and subsequently with fatal toxicoses in India and West Africa. Aflatoxins have also been implicated as a contributory epidemiological factor along with hepatitis B virus in areas of Africa, China, and Southeast Asia where there is an extremely high incidence of liver cancer. Unfortunately, aflatoxin contamination is still widespread, and serious contamination problems have been found in nuts, grains, bread, milk and other foods. See J. E. Linz and J. J. Pestka, *Mycotoxins: Molecular Strategies for Control*, in *Aspergillus: Biology and Industrial Applications* (eds. J. W. Bennett and M. A. Klich, 1992); R. Y. Stanier et al., *The Microbial World* (Fifth Edition, 1986); F. S. Yeh et al., *Cancer Res.* 49, 2506–2509 (1989).

Aspergilli and other fungi are also important agents of disease in both domestic and wild animals. These fungi cause disease both by infection and by intoxication. Infection caused by Aspergilli occurs regularly in poultry, calves, cows, horses and avian species. Infectious fungal agents, especially *A. fumigatus*, are present in almost all environments in which animals live, which results in a wide variety of separate animal groups being prone to diseases caused by fungi. A. C. Pier and J. L. Richard, *Mycoses and Mycotoxicoses of Animals Caused by Aspergilli*, in *Aspergillus, supra*. Mycotoxicoses, the second group of diseases caused by fungi, are caused by the mycotoxins produced by fungal species. Several Aspergillus strains produce mycotoxins that cause diseases of the liver, kidney, and other organs. Approximately one-quarter of the food crops of the world are affected by mycotoxins each year. J. Richard and R. Cole, *Mycotoxins: Economic and Health Risks*, (Council for Agriculture Science and Technology Task Force Report, 1989). There is therefore a huge, worldwide economic cost that arises directly from crop and livestock losses. Elimination of mycotoxins from the food and feed supply would sharply decrease this economic cost.

Numerous approaches to reduction of aflatoxin levels in agricultural commodities have been experimentally assessed. These methods include e.g., mixing and diluting toxin-containing grain lots with aflatoxin-free grains in order to obtain toxin levels within regulatory guidelines; physical methods of separation such as cleaning, density segregation, and preferential fragmentation; solvent extraction; biological inactivation; thermal inactivation; chemical inactivation; soil fumigation; and addition of montmorillonite clay to animal feed. These approaches have been relatively unsuccessful on a commercial scale due to lack of efficacy, economic restraints of the protocols, unacceptable alteration of feed or food quality, or the introduction of potentially deleterious substances. For example, aflatoxins are very heat-stable and are not eliminated by heat treatments. Ammonia treatments will almost eliminate aflatoxins from peanut meal and grains, but may reduce their food value. See Kendrick, *supra*, at 299.

It would therefore be desirable to provide a simple, cost-effective, practical, and safe process by which plants, crops, foodstuffs, and animal feeds can be decontaminated or detoxified, particularly with respect to mycotoxins such as aflatoxins.

SUMMARY OF THE INVENTION

The present invention relates to a method of inhibiting mycotoxin production in plants, crops, foodstuffs, and animal foodstuffs. Accordingly, a first aspect of the invention is a method of inhibiting mycotoxin production in a foodstuff comprising contacting the foodstuff with trans-2-hexenal. In a preferred embodiment of the invention, the foodstuff is contacted with trans-2-hexenal in an amount and under conditions effective to inhibit mycotoxin production.

A second aspect of the invention is a method of inhibiting mycotoxin production on a plant comprising contacting the plant with trans-2-hexenal. In a preferred embodiment of the invention, the plant is contacted with trans-2-hexenal in an amount and under conditions effective to inhibit mycotoxin production. The contacting step of the present invention may occur at any time during the life cycle of the plant, and may also involve contacting the environment in which the plant is grown with trans-2-hexenal.

A third aspect of the invention is a method of inhibiting microbial infection in a plant in need of such treatment, comprising administering to the plant trans-2-hexenal. In a preferred embodiment of the invention, the plant is contacted with trans-2-hexenal in an amount and under conditions effective to limit and treat the infection. The contacting step of the present invention may occur at any time during the life cycle of the plant, and may also involve contacting the environment in which the plant is grown with trans-2-hexenal.

The present invention provides several advantages over methods known in the prior art, in that the active compound of the invention, trans-2-hexenal, is a readily-available natural substance that may also be chemically synthesized. The active compound evaporates quickly and is generally non-toxic. Additionally, the compound of the present invention may be easily administered over a substantial period of time, and administration may be repeated periodically as necessary.

DETAILED DESCRIPTION OF THE INVENTION

As summarized above, the present invention provides a method of inhibiting the production of mycotoxins in plants, crops, foodstuffs and animal feedstuffs (i.e., a "substrate") by contacting the targeted substrate with trans-2-hexenal (also referred to herein as the "active compound"). Further, a method of treating microbial infection in plants by contacting the plants with trans-2-hexenal is also provided.

The structure of trans-2-hexenal, also referred to as (E)-2-hexenal, is known. Trans-2-hexenal, which is responsible for a characteristic "green note" or leaf odor, is distributed in a wide variety of plants. A member of the 6-carbon chain length volatile compounds collectively referred to as leaf aldehydes and leaf alcohols, trans-2-hexenal is produced by green leaves through the lipoxygenase/hydroperoxide (LOX) lyase pathway. W. Deng et al., *J. Agric. Food Chem.* 41, 506–10 (1993). Volatile lipid peroxidation products from the LOX pathway are important for the organoleptic quality of certain plant-derived foods. T. Matoba et al., *J. Agric. Food Chem.* 33, 852–855 (1985). Methods of extracting trans-2-hexenal from plants will be apparent to one skilled in the art. See, e.g., PCT Application No. PCT/US95/02929 (applicant specifically intends that the disclosure of this and all other patent references cited herein be incorporated herein by reference in their entirety). Additionally, trans-2-hexenal may be chemically synthesized, and is available commercially.

In the practice of the present invention, trans-2-hexenal may be administered to a substrate in an essentially pure form. However, it is also within the scope of the invention that trans-2-hexenal may also be administered in combination with other green note, leaf alcohol or leaf aldehyde compounds, especially when trans-2-hexenal and the other green note compounds are used in their naturally-derived form. By "combination" is meant that trans-2-hexenal may be present along with at least one additional green-note compound in the same formulation (e.g., a mixture), or may be administered separately. Examples of additional green note compounds include, but are not limited to, trans-2-hexenol, cis-2-hexenol, trans-3-hexenol, 1-hexanol, n-hexenal, cis-3-hexenal, cis-3-hexenol, cis-3-penten-3-ol, and cis-2-penten-1-ol. Accordingly, it is specifically intended that the term "active compound" encompass both trans-2-hexenal in essentially pure form, and in combination with other green note compounds.

The methods of the present invention are useful for inhibiting mycotoxin production or microbial infection (e.g., the "condition") in that they inhibit the onset, growth, or spread of the condition, cause regression or reduction of the condition, cure the condition, or otherwise improve the general well-being or quality of a substrate afflicted with, or at risk of contracting the condition.

Besides providing a method for inhibiting the above-described conditions, the present invention also provides a method for prophylaxis against such conditions in a substrate, which has had at least one episode of the condition, but which at the time of treatment is not exhibiting signs of the condition. Accordingly, the present invention provides a method for the prophylaxis against mycotoxin production or microbial infection comprising administering to the substrate a prophylactically effective amount of the active compound of the present condition. The forms for administration of the compound in accordance with this method may be the same as utilized for the purpose of actually treating a substrate afflicted by the undesired condition.

An additional useful aspect of the present invention is a method for prophylaxis against even an initial episode of mycotoxin production or microbial infection in a substrate that has never been afflicted with an episode of the condition. In this respect, a substrate that may be at risk for microbial infection or mycotoxin production, even before the onset of an initial episode of the condition, may avoid or delay suffering from the condition by having administered a prophylactically effective amount of the active compound of the present invention. The compound may be administered in the same fashion as in the treatment of substrates already afflicted with the condition.

The method of the present invention has, for practical field application, an advantageous antimicrobial activity spectrum against harmful microbes. As used herein, microbes include fungi, bacteria, protozoae, viruses, and other microorganisms. The present invention has particular utility against phytopathogenic fungi and bacteria. Compounds of the present invention have advantageous curative and preventative properties, and can be used for protecting numerous cultivated plants from both infections caused by microbes and toxins which may be produced by the microbes. With the method of the present invention, it is possible to inhibit or destroy the microbes which occur on plants or on parts of plants (e.g., fruits, blossoms, leaves, stems, tubers, and roots) in different crops of useful plants. At the same time, the parts of plants which grow later are also protected from attack by phytopathogenic organisms, as active compounds used in the present invention have excellent activity against fungi and other microbes which occur in seeds or soil.

Accordingly, the method of the present invention is useful in the treatment of environments in which plants are grown and stored (e.g., soil, greenhouse or barn environments), in order to prevent the growth of fungi and other microbes therein. Other materials useful in the cultivation of plants, such as agricultural equipment and nutritional additives, may also be similarly treated. In one embodiment of the present invention, soil intended for the use of cultivation of plants is treated e.g., fumigated) using the active compounds of the present invention. In another embodiment, soil that ms already being used in the cultivation of plants is treated with the compounds of the present invention. In yet another embodiment, the airspace of a greenhouse in which plants are being cultivated is treated with the active compounds of the present invention.

Within the scope of the present invention, a crop is defined as a plurality of plants that are planted together in an agricultural field. By agricultural field is meant a common plot of soil or a greenhouse or barn, with the determinative feature typically being that a common population of microbes infect that crop of plants.

As a method of plant protection, the method of the invention has an advantageous activity spectrum for practical application in agriculture for protecting cultivated plants without damaging the plants by harmful side-effects.

In addition, the method of the present invention can be successfully used for inhibiting microbial infection and mycotoxin production in storable goods of vegetable, fungal (e.g., mushrooms) or animal origin. Accordingly, the antimicrobial methods for controlling phytopathogenic microbes may also be used for the preventive treatment of stored goods of vegetable and animal origin to protect them from attack by such microbes. Furthermore, the active compound of the present invention may be used to treat environments in which such goods are stored and materials which may come into contact with such stored goods. In one embodiment of the invention, a storage environment that is particularly susceptible to mycotoxin production or microbial infection for any reason (e.g., temperature or humidity conducive to the growth of microbes) is treated using the method of the present invention in order to prevent the growth of fungi and other microbes therein.

Within the scope of this invention, storable goods will be understood as meaning natural substances of plant and/or animal origin and products obtained therefrom by further processing, for example the plants listed below whose natural life cycle has been interrupted and the parts thereof (e.g., stalks, leaves, tubers, seeds, fruit grains). These plants and the parts thereof may be, for the purposes of this invention, in freshly harvested or further processed (e.g., predried, moistened, crushed, ground, roasted) form.

Examples of natural products of animal origin are, in particular, dried meat and processed fish products such as dry-cured meat, frozen or thawed meat, dry-cured fish, meat extracts, bone meal, fish meal and animal dry feeds.

The storable goods treated with compounds of the invention are given protection from attack by fungi and other undesired microorganisms. The formation of toxic and in some cases carcinogenic fungal metabolites (e.g. aflatoxins and ochratoxins) is inhibited, the goods are protected from deterioration, and their quality is maintained over a long period of time. The method of the invention can be applied to all forms of dry and moist goods which are susceptible to attack by microorganisms such as yeast, bacteria, and, in particular, fungi.

For the purpose of this invention, the term "foodstuff" includes both solid and liquid consumable materials which usually do, but need not, have nutritional value. The term is also specifically intended to encompass products that may not be ingested, but may come into contact with a consumer nonetheless (e.g., tobacco, topical therapeutics or cosmetics). It is specifically intended that foodstuffs suitable for both human and animal consumption are embraced by the scope of the invention.

The term "animal feedstuff," for the purpose of the present invention, refers to any natural and processed or otherwise modified organic materials which are susceptible to biodeterioration and which can be consumed by animals or birds for nourishment. Examples of such organic materials range from freshly harvested grains to pelletized feeds. In one embodiment of the present invention, animal feeds for use in the instant invention are poultry, fish and livestock feeds.

The method of the present invention is useful in the control of fungi, preferentially phytopathogenic fungi, and more preferentially in mycotoxin-producing fungi. Examples of these fungi include but are not limited to fungi of the genera Penicillum (e.g., *P. viridicatum, P. verrucosum, P. patulum, P. notatum, P. expansum, P. claviform, P. cyclopium, P. roquefortii, P. commune, P. purpurescens*, and *P. variabile*); Aspergillus (e.g., *A. flavus, A. parasiticum, A. nomius, A. chevalieri, A. ochraeus, A. alutaceus, A. alliaceus, A. melleus, A. ostianus, A. petrakii, A. sclerotiorum, A. sulphureus, A. niger, A. oryzae, A. terreus, A. versicolor, A. fumigatus, A. nidulans,* and other Aspergillus species); Cladosporium; Rhizopus (e.g., *R. leguminicola*); Fusarium (e.g., *F. oxysporum, F. graminarium, F. moniliformae, F. poa,* and *F. sporotrichiodes*); Helminthosporium; Nigrospora; Claviceps (e.g., *C. purpurea*); Stachybotryis (e.g., *Stachybotryis atra*); Pithomyces (e.g., *P. chartarum*); Gliocladium; and Alternaria species.

The method of the invention is useful in inhibiting the production of a wide variety of mycotoxins, including but not limited to: aflatoxins (e.g., aflatoxins B1, B2, G1 and G2); cyclopiazonic acid; gliotoxins; citreoviridin; oxalic acid; penicillic acid; the trichothecenes (e.g. 4-deoxynivalenol, T-2 toxin); fumonisin; stachybotrytoxin; zearalenone (F2 toxin); the ochratoxins (e.g. ochratoxin-A); sporidesmin; slaframine; penitrem A; PR toxin; tenuazonic acid; patulin; sterigmatocystin; ergotamine; and ergometrine.

Target crops to be protected within the scope of the present invention comprise the following species of plants, cited by way of example without any restriction to the field of use within the scope of the invention: cereals (wheat, barley, rye, oats, rice, sorghum, and the like); beets (sugar beet and fodder beet) pomes, drupes, and soft fruit (apples, pears, plums, peaches, almonds, cherries, strawberries, raspberries, and blackberries); leguminous plants (beans, lentils, peas, and soybeans); oil plants (rape, mustard, poppy, olives, sunflowers, coconut, castor oil plants, cocoa beans, and peanuts); cucumber plants (cucumber, melons); fiber plants (cotton, flax, hemp, and jute); citrus fruit (oranges, lemons, grapefruit, and mandarins); vegetables (spinach, lettuce, asparagus, cabbages, carrots, onions, tomatoes, potatoes, and paprika); lauraceae (avocados, cinnamon, cinnamon, and camphor) and plants such as maize, tobacco, nuts, coffee, sugar cane, tea, hops, vines, bananas, grass, hay, natural rubber plants, and ornamentals.

In treating a substrate by the method of the present invention, the amount of active compound used will vary according to the condition being treated, the general health or quality of the substrate, and the extent of treatment desired. It is preferred that the active compound is applied to the substrate in a concentration effective to prevent, inhibit, control or otherwise reduce the amount of microbial infection or mycotoxin production in the substrate. In a preferred embodiment of the invention, the active compound is present in a concentration of at least 25 ng/L of the volume of the area being treated, preferably in a concentration of at least 35 ng/L, and most preferably in a concentration of at least 50 ng/L. The active compounds may be administered in concentrations of up to 1 µg/L and even up to 100 µg/L or more. As a general rule, the concentration of active compound effective in treating mycotoxin production or microbial infection in vivo or in situ will be at least 5 times (5×) and more preferably, at least 10 times (10×) as much as the concentration found to be effective under in vitro conditions.

Substrates may be treated with the active compound of the present invention by a number of means which will be apparent to the practitioner skilled in the art of integrated pest management, including fumigation and spraying. The selection of techniques and equipment useful in the application of the active compounds of the present invention will also be apparent to the skilled practitioner. A preferred method of applying a compound of the present invention or an agrochemical composition containing the compound, is foliar application. In one embodiment of the invention, the active compound is in the vapor phase and is contacted to the substrate in a closed or sealed environment, such as an airtight barn or greenhouse. An alternative embodiment of the method of invention comprises spraying or wetting the substrate with a liquid formulation, or mixing the substrate with a formulation containing the active compound. In yet another embodiment, the active compound is present in a solid formulation, which is placed in an environment in which treatment is desired and allowed to evaporate.

The number of applications of the active compound and the rate of application will depend on the extent or risk of infestation by the corresponding pathogen (species of microorganisms). The selection of the appropriate frequency and duration of application will be within the skill of one in the art. It is specifically intended that the active compound of the present invention may be applied repeatedly and periodically to the same substrate as desired, in order to prevent or inhibit mycotoxin production or microbial infection for a desired length of time. The active compound may also be applied to seeds, and in special cases, further types of application are also possible, e.g. selective treatment of the plant sites or buds.

The active compound is normally applied in the form of a formulation and can be applied to the crop area (e.g., the soil), plant or substrate to be treated, simultaneously or in succession with other compounds. These other compounds can be both fertilizers or micronutrient donors, or other preparations that influence plant growth. They may be selective herbicides, insecticides, fungicides, bactericides, nematicides, molluscicides or mixtures of several of these preparations, if desired together with further carriers, surfactants or application-promoting adjuvants customarily employed in the art of formulation. In one embodiment of the invention, the active compound is present in an aqueous formulation in a concentration of less than 1% by weight of the total formulation, and preferably in a concentration of less than 0.1% by weight of the total formulation.

Suitable carriers and/or adjuvants may be solid or liquid and include natural or regenerated mineral substances, solvents, dispersants, wetting agents, tackifiers, thickeners, binders or fertilizers.

It is specifically intended that treatment of plants and crops with the active compound of the present invention be utilized both prior to harvest (pre-harvest) and after harvest (post-harvest) of the plant. In a preferred embodiment of the invention, plants are treated with the active compound prior to harvest, while growing in their natural state. In an alternative embodiment of the invention, plants or other substrates that are already in a post-harvest stage, such as in storage prior to distribution, are contacted with the active compound.

The present invention is more fully illustrated by the following examples, which are set forth to illustrate the present invention and are not to be construed as limiting thereof. In the following examples, mm means millimeter, ft means feet, µg means micrograms, ng means nanograms, L means liters, and mL means milliliters.

EXAMPLE 1

In Vitro Inhibition of Microbes with Trans-2-Hexenal

The following microbes were screened for growth inhibition by trans-2-hexenal: *Aspergillus flavus*, *Penicillum notatum*, *Fusarium oxysporum*, *Alternaria alternata*, and *Cladosporium* species (all fungi); *E. Coli*, *B. subtilis*, *Pseudomonas aeruginosa* and *Agrobacteria tumefaciens* (all bacteria); and *Saccharomyces cerevisiae* (yeast).

Initially, natural trans-2-hexenal was obtained by kale green note processing by using a method similar to that described in PCT Application No. PCT/US95/02929. Synthetic trans-2-hexenal (Aldrich Chemicals) were screened and found to have a similar activity profile to the natural trans-2-hexenal. In subsequent experiments, synthetic trans-2-hexenal was used.

Microbial cultures were grown in a lawn on a 35 mm×10 mm petri dish, with nutrient agar for bacterial strains and potato dextrose agar for yeast and fungi. Each plate was then placed inside a 100 mm petri dish under sterile conditions. On the upper lid of the larger plate a 3 mm diameter hole was made, and a rubber valve fixed to it. The upper lid of the smaller plate was removed and used as a test solution reservoir. One mL of sterile deionized water was added to the plate and either trans-2-hexenal or cis-3-hexenol (test solution) at varying concentrations were added. Quantities of the test solution were determined by direct sampling of the headspace of the bioassay dishes and analysis with gas chromatography.

After addition of the test solution, the lid to plate was sealed with two layers of parafilm. Plates containing a bacterial lawn were incubated at 35° C. for 48–72 hours, while yeast and fungi plates were incubated at 26° C. for 72 hours up to one week. After incubation, inhibition of growth was noted.

Trans-2-hexenal completely inhibited the growth of *A. flavus*, *P. notatum*, *A. alternata*, *F. oxysporum*, *Cladosporium* species, *B. subtilis* and *A. tumefaciens* at a concentration of 8 ng/L space. At this concentration, the growth of the remaining microbes were not inhibited.

In comparison, cis-3-hexenol did not inhibit the growth of any of the microbes tested, even at a concentration of 100 µg/L space.

These results indicate that trans-2-hexenal is effective against a wide variety of fungal and bacterial microorganisms that are known to cause both disease-causing infection and mycotoxin production. As such, trans-2-hexenal may effectively be applied to a broad range of materials susceptible to such infestation, including plants, cultivation environments and materials, and storable goods and storage environments.

EXAMPLE 2

In Vivo Inhibition of Fungal Growth by Trans-2-Hexenal

Flue-cured tobacco was stored in 5 ft×5 ft air tight tobacco barns, and allowed to become infested with a variety of tobacco barn fungi. Different amounts of trans-2-hexenal were administered to each barn as a fumigant and allowed to dissipate over a period of 2–4 hours, after which the number of colony-forming units per leaf of tobacco was noted using a standard dilution plate count method. The results of this experiment are presented below.

| Barn Number | Amount of Trans-2-Hexenal Administered | cfu/g tobacco leaf |
| --- | --- | --- |
| 1 | 0 (control) | 40 × 10$^4$ |
| 2 | 50 g | 10 × 10$^2$ |
| 3 | 100 g | 10 × 10$^2$ |

This example illustrates that plants and other materials held in storage that are susceptible to infection by pathogenic as well as saprophytic microorganisms may effectively be treated by the methods of the present invention.

In the specification and examples, there have been disclosed preferred embodiments of the invention. Although specific terms are employed in these examples, they are used in a generic and descriptive sense only and not for the purpose of limitation, the scope of the invention being defined by the following claims.

That which is claimed is:

1. A method of inhibiting mycotoxin production in a foodstuff in storage comprising contacting the foodstuff with trans-2-hexenal in an amount effective to inhibit mycotoxin production, whereby the mycotoxin is produced by a fungus selected from the group consisting of Aspergillus, Fusarium, Penicillum and Cladosporium genera.

2. The method according to claim 1, whereby the mycotoxin is an aflatoxin.

3. The method according to claim 1, whereby the foodstuff is animal feed.

4. The method according to claim 1, whereby said contacting step comprises contacting the foodstuff with trans-2-hexenal in the vapor phase.

5. The method according to claim 1, whereby said contacting step comprises contacting the foodstuff with trans-2-hexenal in the liquid phase.

* * * * *